(12) United States Patent
Mirov et al.

(10) Patent No.: US 10,688,255 B2
(45) Date of Patent: Jun. 23, 2020

(54) AIR SHOT DETECTION

(71) Applicant: Verily Life Sciences LLC, Mountain View, CA (US)

(72) Inventors: Russell Mirov, Los Altos, CA (US); Benjamin David Krasnow, Redwood City, CA (US); Peter Howard Smith, Pacificia, WA (US); Travis Deyle, San Jose, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 339 days.

(21) Appl. No.: 15/498,903

(22) Filed: Apr. 27, 2017

(65) Prior Publication Data

US 2017/0312455 A1   Nov. 2, 2017

Related U.S. Application Data

(60) Provisional application No. 62/329,605, filed on Apr. 29, 2016, provisional application No. 62/434,662, filed on Dec. 15, 2016.

(51) Int. Cl.
*A61M 5/36* (2006.01)
*A61M 5/315* (2006.01)
(Continued)

(52) U.S. Cl.
CPC .......... *A61M 5/365* (2013.01); *A61M 5/3146* (2013.01); *A61M 5/31511* (2013.01);
(Continued)

(58) Field of Classification Search
CPC ................ A61M 5/365; A61M 5/3146; A61M 5/31511; A61M 5/31568; A61M 5/486
See application file for complete search history.

(56) References Cited

U.S. PATENT DOCUMENTS 5,720,733 A   2/1998   Brown
6,368,314 B1  4/2002   Kipfer et al.
(Continued)

FOREIGN PATENT DOCUMENTS

CA   2 604 498 A1   10/2006
EP   2 777 731 A1    9/2014
(Continued)

OTHER PUBLICATIONS

International Search Report and Written Opinion from the International Searching Authority dated Mar. 5, 2018, for International Application No. PCT/US2017/063768, filed Nov. 29, 2017, 16 pages.
(Continued)

*Primary Examiner* — Catherine T. Rastovski
(74) *Attorney, Agent, or Firm* — Christensen O'Connor Johnson Kindness PLLC

(57) ABSTRACT

A medication injection device includes a barrel and a plunger disposed to dispense a fluid from the barrel. A dosage tracking system is coupled to output data indicative of the fluid dispensed. A controller is disposed within the medication injection device and coupled to receive the data from the dosage tracking system. The controller includes logic that when executed by the controller causes the controller to perform operations including determining, based on the data, whether an air shot event occurred while dispensing the fluid.

25 Claims, 9 Drawing Sheets

(51) Int. Cl.
*A61M 5/31* (2006.01)
*A61M 5/48* (2006.01)

(52) U.S. Cl.
CPC ......... *A61M 5/31568* (2013.01); *A61M 5/486* (2013.01); *A61M 2205/0216* (2013.01); *A61M 2205/18* (2013.01); *A61M 2205/215* (2013.01); *A61M 2205/33* (2013.01); *A61M 2205/3344* (2013.01); *A61M 2205/3368* (2013.01); *A61M 2205/3375* (2013.01); *A61M 2205/3569* (2013.01); *A61M 2205/3584* (2013.01); *A61M 2205/3592* (2013.01); *A61M 2205/50* (2013.01); *A61M 2205/52* (2013.01); *A61M 2205/581* (2013.01); *A61M 2205/583* (2013.01); *A61M 2205/587* (2013.01); *A61M 2205/8206* (2013.01); *A61M 2205/8212* (2013.01)

(56) References Cited

U.S. PATENT DOCUMENTS

| | | | |
|---|---|---|---|
| 8,708,957 B2 | 4/2014 | Jespersen et al. | |
| 9,314,573 B2 | 4/2016 | Nielsen et al. | |
| 2001/0034506 A1 | 10/2001 | Hirschman et al. | |
| 2007/0060820 A1 | 3/2007 | Lofgren et al. | |
| 2007/0235083 A1* | 10/2007 | Dlugos | A61F 5/0003 137/223 |
| 2011/0270214 A1 | 11/2011 | Jorgensen et al. | |
| 2012/0195182 A1 | 8/2012 | Pommereau et al. | |
| 2013/0072897 A1 | 3/2013 | Day et al. | |
| 2014/0288408 A1 | 9/2014 | Deutsch | |
| 2015/0165114 A1* | 6/2015 | Grant | A61M 5/14586 604/151 |
| 2015/0202375 A1 | 7/2015 | Schabbach et al. | |
| 2015/0217059 A1 | 8/2015 | Ashby et al. | |
| 2015/0273129 A1* | 10/2015 | Freeman | A61M 1/3633 210/698 |
| 2015/0289895 A1 | 10/2015 | Gomi et al. | |
| 2016/0022539 A1 | 1/2016 | Daines | |
| 2016/0030663 A1* | 2/2016 | Adaniya | A61M 5/16877 604/28 |
| 2016/0213856 A1* | 7/2016 | Despa | A61M 5/31568 |
| 2018/0001009 A1* | 1/2018 | Crawford | A61M 1/3661 |
| 2019/0022306 A1* | 1/2019 | Gibson | A61M 5/142 |

FOREIGN PATENT DOCUMENTS

| | | | |
|---|---|---|---|
| WO | 2007/000680 A2 | | 1/2007 |
| WO | 2007024193 A2 | | 3/2007 |
| WO | 2010/052275 A2 | | 5/2010 |
| WO | 2016/007935 A2 | | 1/2016 |
| WO | WO 2016/062605 | * | 4/2016 |
| WO | WO 2016/062605 A1 | | 4/2016 |
| WO | 2016/122974 A1 | | 8/2016 |

OTHER PUBLICATIONS

International Application No. PCT/US2017/030068—International Search Report and Written Opinion dated Aug. 11, 2017, 20 pages.
International Preliminary Report on Patentability and Written Opinion dated Oct. 30, 2018 for International Application No. PCT/US2017/023653, filed Mar. 22, 2017, 8 pages.
International Preliminary Report on Patentability and Written Opinion dated Oct. 30, 2018 for International Application No. PCT/US2017/025085, filed Mar. 30, 2017, 9 pages.
International Preliminary Report on Patentability and Written Opinion dated Oct. 30, 2018 for International Application No. PCT/US2017/030068, filed Apr. 28, 2017, 14 pages.
English Translation of Chinese Office Action for corresponding Chinese Patent Application No. 201790000809.1, dated Jul. 11, 2019, pp. 1-3.
English Translation of Chinese Office Action for corresponding Chinese Patent Application No. 201790000809.1, dated Sep. 4, 2019, 2 pages.
European Office Action, dated Mar. 23, 2020, in corresponding European Patent Application No. 17722350.0-1122, 4 pages.

* cited by examiner

AIR SHOT DETECTION

REFERENCE TO RELATED APPLICATIONS

This application claims the benefit of U.S. Provisional Application No. 62/329,605, filed on Apr. 29, 2016, and U.S. Provisional Application No. 62/434,662, filed on Dec. 15, 2016, the entire contents of which are hereby incorporated by reference herein.

TECHNICAL FIELD

The present disclosure relates generally to the field of tracking the administration of medication, and more particularly, apparatus and methods for tracking the administration of medication by medication injection devices.

BACKGROUND INFORMATION

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range. Currently, there are a limited number of methods or devices for automatically tracking the drug administration without requiring the user to manually measure and record the volume, date, and time.

A variety of glucose injection syringes/pens have been developed, but there is much room for significant advancement in the technology. For example, current insulin pens are often disposable, but do not include dosage tracking. A smaller portion of the market is composed of reusable pens which are more expensive, and still don't include good dosage tracking or automatic air shot detection.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1:
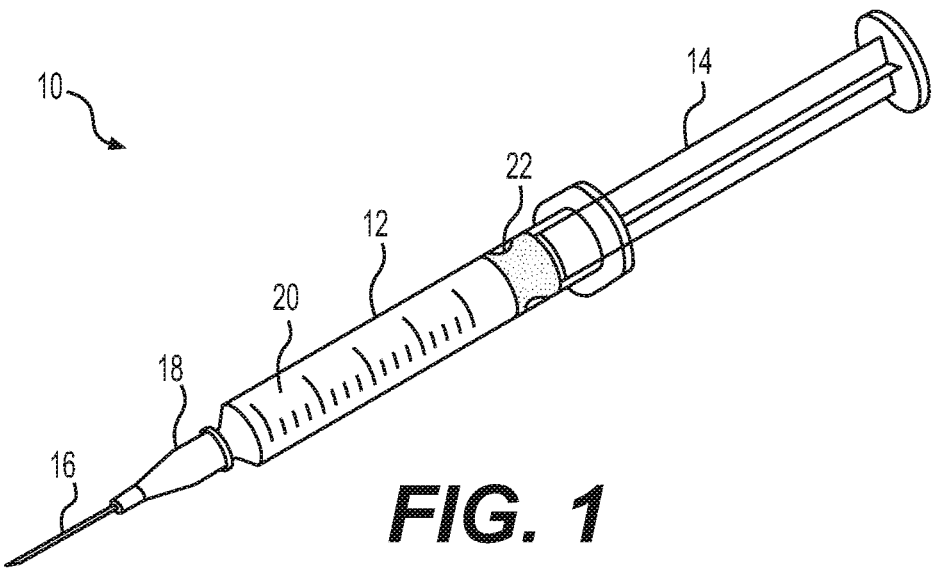
FIG. 1 is a perspective view of a medication injection device, which includes a plunger head, according to an exemplary embodiment.

Embodiments of an apparatus and method for air shot detection are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The present disclosure is directed at detecting an "air shot" (or "prime shot") from a medical injection device (e.g., injection pen or syringe) in order to accurately measure the amount of medication a user injects. Prior to injecting a drug such as insulin typically the user will perform an air shot to remove bubbles or debris from the solution. An air shot includes the user dispensing fluid into the air prior to an injection event into the body. Failure to differentiate, whether the volume dispensed is part of an air shot or injection could lead to more medication than was actually injected being recorded, and this can lead to inaccurate medication injection records.

In some embodiments this air shot detection may be achieved with a plunger head for a medication injection device. The plunger head may include an ultrasonic transducer that sends and receives ultrasonic signals and an antenna. The plunger head may also include a controller that interfaces with the ultrasonic transducer and the antenna and a power source that powers the controller and the ultrasonic transducer. The controller may include logic that when executed by the controller causes the controller to perform operations including receiving data from the ultrasonic transducer and calculating a volume displaced by the plunger head based on the data, and determining, based in part on the data received from the ultrasonic transducer, whether the volume displaced was an air shot.

Other embodiments of the present disclosure may relate to a method of tracking injections of a medication delivered by a medication injection device. The method may include depressing a plunger of the medication injection device and sending and receiving ultrasonic signals from a plunger head installed within a barrel of the medical injection device. The method may also include measuring the time it takes for the signals to travel through the medication to an end of the barrel and return to the plunger head (i.e., time of flight). The method may further include calculating the distance the plunger head travels based on a change in the time and calculating a volume dispensed based on the distance the plunger head travels. Also the method may include measuring a distance travelled by the plunger head based upon the time of flight of the ultrasonic signals and determining that the air shot event occurred while dispensing the fluid when the distance travelled by the plunger head is below a threshold distance.

In other embodiments, the present disclosure is directed to devices and methods of identifying an air shot from a medication injection device. The method may include calculating a quantity of the medication dispensed from the medication injection device. The devices/methods may further include identifying an air shot of medication using an algorithm (e.g., logic stored in a controller), where the algorithm identifies the air shot event as including a fluid dispensing event where the fluid is deemed not to have been injected into a body (among other events/occurrences). The one or more air shot events may include at least one of an air shot volume event, air shot pattern event, air shot pressure event, a bubble dislodge event, a fluid mixing event, and/or air shot velocity event.

FIG. 1 shows a perspective view of a medication injection device in the form of a syringe 10 designed for ejecting a fluid. Syringe 10 may include a barrel 12, a plunger 14, a needle 16, and a hub 18 connecting needle 16 to barrel 12. Barrel 12 may be configured to contain a fluid, for example, a medication 20 and syringe 10 may be configured to dispense medication 20 from needle 16 when plunger 14 is depressed. A standard syringe usually contains a plunger head at the end of the plunger that seals the top of the barrel and forces the fluid out the needle when the plunger is depressed. The plunger head for a standard syringe is usually just a piece of molded rubber.

For syringe 10 shown in FIG. 1, the standard plunger head has been replaced with a smart or intelligent plunger head 22 (e.g., a dosage measurement system) that is configured to measure and register the quantity of medication 20 administered and the time and date of administration. Plunger head 22 may be installed in a standard syringe by withdrawing plunger 14 and removing the standard plunger head and installing smart plunger head 22. In some embodiments, syringe 10 may be manufactured and supplied with a smart plunger head 22 preinstalled. Smart plunger head 22 may be referred herein as either smart plunger head 22 or plunger head 22.

Plunger head 22 may be sized to correspond with the size of barrel 12. For example, plunger head 22 may be formed to fit any size syringe. For example, plunger head 22 may be sized to fit a 1 ml, 2 ml, 3 ml, 5 ml, 10 ml, 20 ml, 30 ml, or 50 ml syringe.

Figure 2:
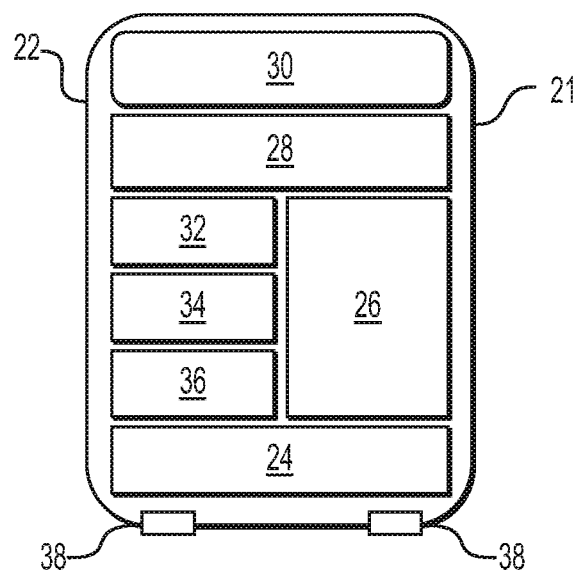
FIG. 2 is a schematic of the plunger head of FIG. 1, according to an exemplary embodiment.

FIG. 2 shows a schematic of plunger head 22, according to an exemplary embodiment. Plunger head 22 may include a transducer 24, a controller 26, a power source 28, and an antenna (e.g., for near field communication (NFC) or a transceiver 30 (e.g., for BLUETOOTH low energy (BLE) communication). In some embodiments, plunger head 22 may also include a temperature sensor 36. Temperature sensor 36 may be configured to measure the ambient temperature, which may be generally representative of a temperature of plunger head 22 and/or medication 20.

Transducer 24 may be an ultrasonic transducer configured to send and receive ultrasonic signals. Controller 26 may be programmed with instructions to control the overall operation of the plunger head. Transceiver 30 may be configured to wirelessly communicate with a remote device (e.g., a smart phone, a glucose monitor, an insulin pump, or a computer) using one or more wireless communication methods. The one or more wireless communication methods may include, for example, radio data transmission, Bluetooth, BLE, near field communication (NFC), infrared data transmission, electromagnetic induction transmission, and/or other suitable electromagnetic, acoustic, or optical transmission methods. Power source 28 may be configured to power transducer 24, controller 26, transceiver 30, temperature sensor 36, and other electronic components of plunger head 22.

In some embodiments, as shown in FIG. 2, the components of plunger head 22 may be at least partially encapsulated in an elastomer 21 (e.g., rubber, ethylene propylene (EPM), Nitrile (NBR), ethylene propylene diene (EPDM), polybutadiene, or polisoprene) that is shaped to define plunger head 22.

Figure 3:
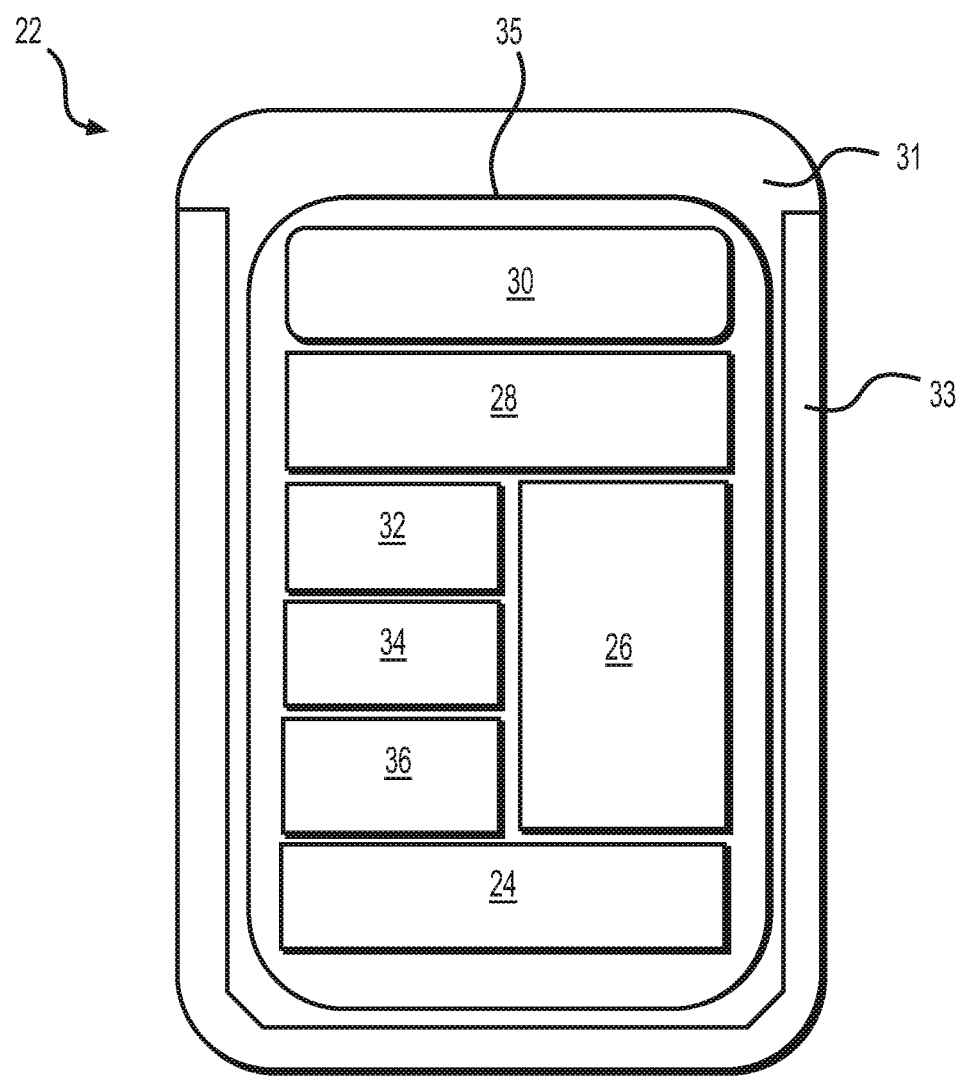
FIG. 3 is a cross-sectional schematic illustrating another embodiment of the plunger head of FIG. 1, according to an exemplary embodiment.

In some embodiments, plunger head 22 may formed of a plurality of components. For example, plunger head 22 may be formed of a first component 31 and a second component 33 that may be fixedly or releasably coupled together such that first component 31 and second component 33 may form plunger head 22, as shown in FIG. 3. First component 31 and second component 33 may each take a variety of shapes. FIG. 3 shows a cross-section of one illustrative example where first component 31 may be shaped to define a plug shape while second component 33 may be shaped to define a bucket shape configured to receive the plug shaped first component 31. When installed in barrel 12, plunger head 22 may be oriented such that second component 33 sits below first component 31 such that second component 33 may separate first component 31 from medication 20 contained within barrel 12. As a result, contact with medication 20 within barrel 12 may be limited to second component 33 (i.e., first component 31 may be prevented from contacting medication 20). Such an arrangement may be advantageous because first component 31 and second component 33 may be manufactured from different materials if desired and the available options of materials for first component 31 may be greater because compatibility with medication 20 may be eliminated as a consideration. Second component 33 may be manufactured from elastomers or other materials commonly used to manufacture plunger heads thus reducing or eliminating compatibility concerns, which may reduce and simplify regulatory hurdles and testing. First component 31 may be manufactured from the same material as second component 33 or from different materials including those which may not be compatible with medication 20. For example, second component may be formed of an elastomer (e.g., butyl rubber) while first component may be formed of another plastic, elastomer, or rubber (e.g., silicone rubber).

In some embodiments, as shown in FIG. 3, the electronic components (e.g., transducer 24, controller 26, power source 28, transceiver 30, and temperature sensor 36) may be housed in first component 31 while second component 33 may be a simple elastomer mold or liner designed to separate first component 31 from medication 20. In other words, the electronic components may be isolated from medication 20 within first component 31. In some embodiments, transducer 24, transceiver 30, controller 26, and power source 28 may be plate cylindrically shaped and arranged in a pancake stack configuration within first component 31.

The thickness of second component 33 may vary. For example, in some embodiments, the thickness of second component may be about 0.5 millimeters, about 0.6 millimeters, about 0.7 millimeters, about 0.8 millimeters, about 0.9 millimeters, about 1 millimeter, about 1.1 millimeter, greater than about 1.1 millimeter, or less than about 0.5 millimeters.

In some embodiments, second component 33 may be preinstalled in barrel 12 and supplied with syringe 10 while first component 31 may be supplied separately and configured to get inserted into second component 33 while it sits in barrel 12. This arrangement can facilitate the reuse of first component 31 which may house the electronic components. In some embodiments, first component 31 may be coupled to plunger 14 in order to facilitate easy removal of first component 31 after use.

In some embodiments, as shown in FIG. 3, first component 31 may include, among other things, a structural support system 35. Structural support system 35 may be designed to prevent unintended deformation of first component 31 so that mechanical tolerances may be maintained with desired ranges. In addition, structural support system 35 may be designed to protect (e.g., prevent damage) of the electronic components due to compressive forces applied to plunger head 22 by plunger 14 when medication 20 is being injected. An upper surface of structural support system 35 may be designed to function as a "push plate" for plunger 14 and may be designed to uniformly distribute the compressive forces applied by plunger 14.

Structural support system 35 may be, for example, a rigid skeleton, cylinder, container, or frame work that surrounds or encloses one or more of the electronic components. Although FIG. 3 shows structural support system 35 surrounding all the electronic components, it is contemplated that in some embodiments, less than all or a portion of the electronic components may be contained within or surrounded by a boundary of structural support system 35. In some embodiments, first component 31 may be encapsulated, over-molded, or sealed within a coating (e.g., elastomer, silicone, plastic, or rubber coating).

In some embodiments, one or more of the electronic components may be exposed from first component 31. For example, in some embodiments, a portion of transducer 24 may be exposed from the bottom of first component 31 so that when first component 31 is inserted within second component 33, it mates flush with second component 33.

In some embodiments, first component 31 may also be designed to facilitate proper positioning and orientation of one or more of the electronic components. For example, the shape of first component 31 and second component 33 may be such that when first component 31 is inserted into second component 33, transducer 24 may be pointed generally down a center of barrel 12 when installed. In some embodiments, second component 33 may also be designed to facilitate proper orientation of antenna/transceiver 30 when receiving first component 31.

Structural support system 35 may be made generally semi-rigid or rigid and may be formed of a variety of different materials, for example, plastic, elastomers, composites, metals, or combinations thereof.

In some embodiments, first component 31 may also be arranged to provide additional functionality including, for example, power source 28 (e.g., battery). For example, power source 28 may be positioned such that when no compressive forces are applied to first component 31, then there is no electrical contact between power source 28 and the electronic components, thereby keeping the other electronic components powered down (i.e., conserving power). But when compressive forces are applied to first component 31, power source 28 or one or more of the other electronic components may be moved and brought into electrical contact thereby powering up. In other words, in some embodiments, power source 28 may be positioned within first component 31, such that the compressive force applied by plunger 14 acts as an off/on switch, which initiates (e.g., wakes up or powers up) the electronic components of plunger head 22.

Separating plunger head 22 into first component 31 (that house the electronic components and second component 33 (that contacts the medication) may provide additional advantages. For example, a challenge with monolithic encapsulating or overmolding of electronic components is that the process usually exposes the electronic components to higher temperatures during both the molding step and later sterilization step(s), which may damage the electronic components, in particular, power source 28 (e.g., the battery). By splitting plunger head 22 into separate components (i.e., first component 31 and second component 33), a lower temperature (e.g., about 60 degrees Celsius or less) series of steps for manufacturing and sterilization can be employed for first component 31, which houses the electronic components, while a higher temperature (e.g., greater than about 60 degrees Celsius) series of steps for manufacturing and sterilization can be employed for second component 33, which contacts medication 20. The first component 31 and second component 33 may then be attached (e.g., by adhesive, bonding, or friction), or another attachment means to form a completed sealed and sterile plunger head 22.

Although the multiple component arrangements (e.g., first component 31 and second component 33) is described herein with reference to plunger head 22, it is contemplated that this multiple or separate component arrangement may be utilized in other applications where electronic components are being packaged (e.g., encapsulated or over-molded) for applications of use where they are alongside sensitive materials (e.g., liquids, medications, chemicals, etc.).

Figure 4:
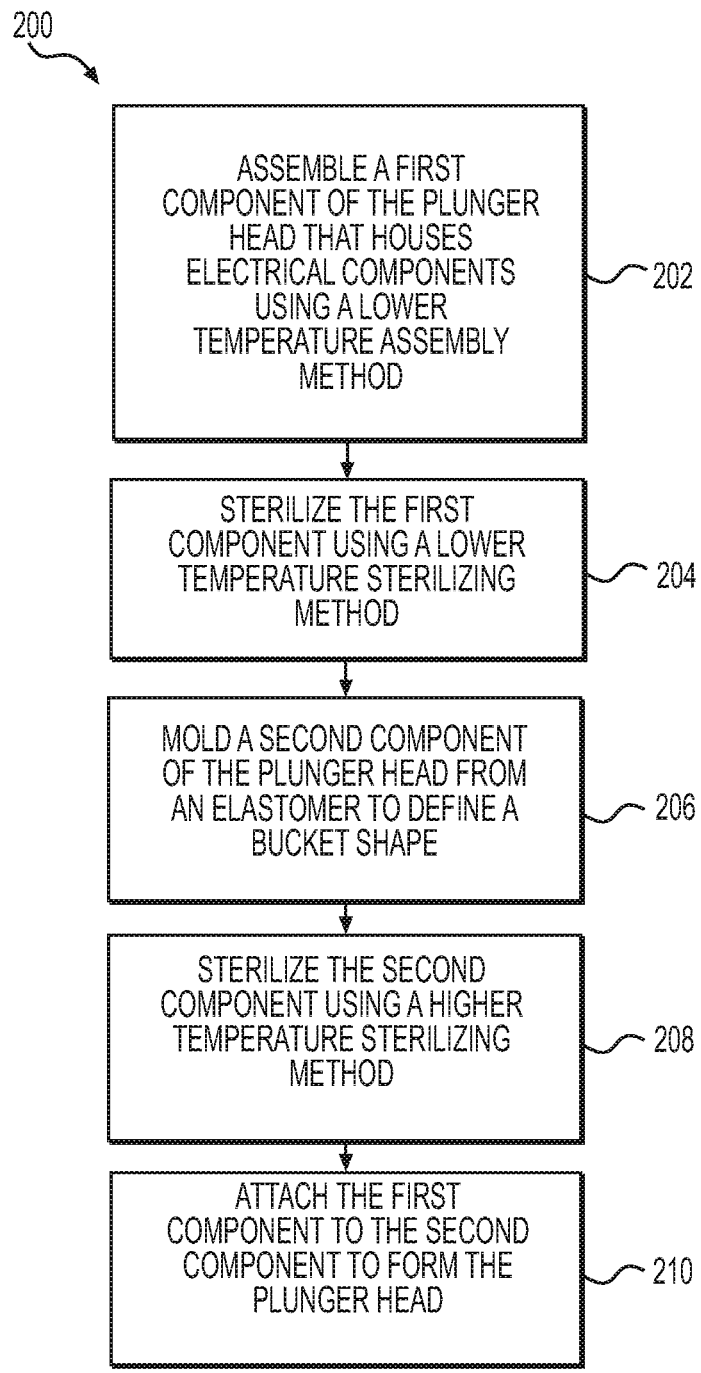
FIG. 4 is a flow chart illustrating a method of manufacturing the plunger head of FIG. 3, according to an exemplary embodiment.

A method 200 of manufacturing plunger head 22 formed of first component 31 and second component 33 will now be explained with reference to FIG. 4. Method 200 may include, at step 202, assembling first component 31 of plunger head 22, which houses the electronic components, using a lower temperature assembly method. Method 200 may also include, at step 204, sterilizing first component 31 using a lower temperature sterilization method. Method 200 may also include, at step 206, molding second component 33 of plunger head 22 from an elastomer to define, for example, a bucket shape). Method 200 may also include, at step 208, sterilizing a second component 33 using a higher temperature sterilization method. Method 200 may also include, at step 210, attaching first component 31 to second component 33 to form plunger head 22. First component 31 and second component 33 may then be attached (e.g., by adhesive, bonding, or friction), or another attachment means to form a completed seal and sterile plunger head 22.

Figure 5:
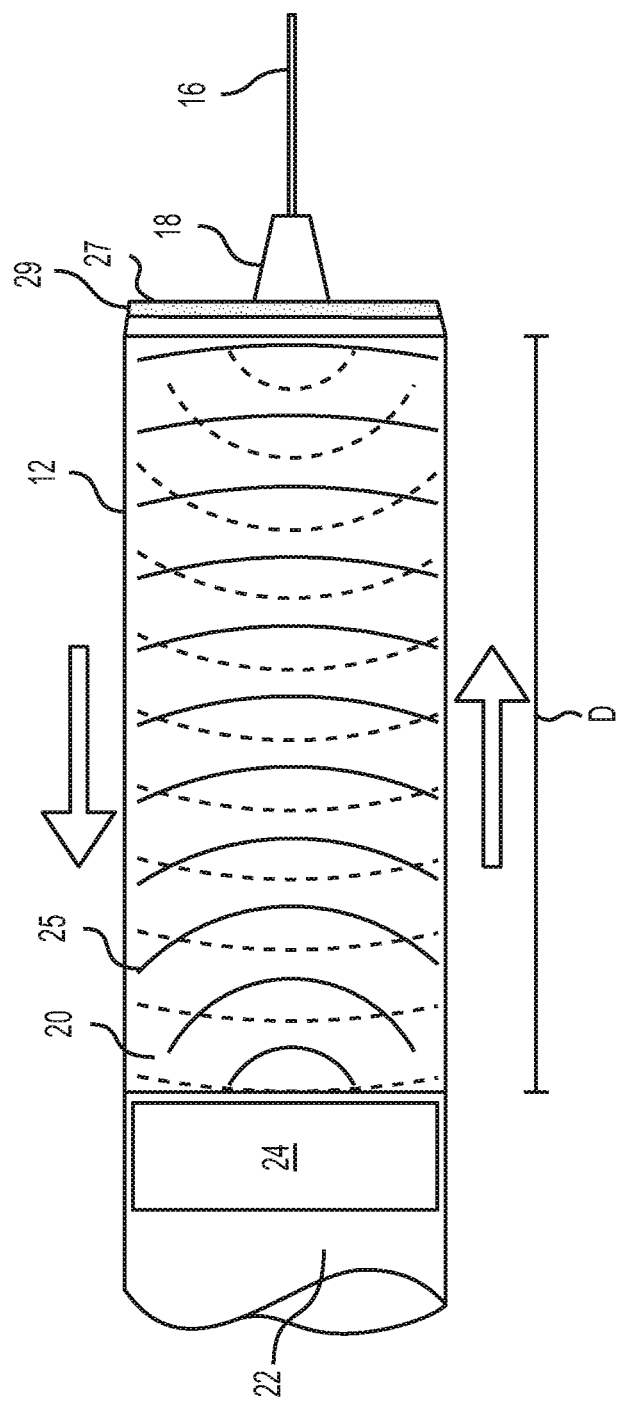
FIG. 5 is a schematic illustrating the behavior of ultrasonic signals transmitted by the plunger head of FIG. 2 or 3, according to an exemplary embodiment.

Transducer 24 may be an actuator, piezoelectric element, or speaker-like voice coil configured to generate and send a pressure wave or ultrasonic signal. Transducer 24 may be sized to be slightly smaller than the inner diameter of barrel 12. As shown in FIG. 5, transducer 24 may be configured to generate ultrasonic signals 25 (e.g., radiated sound energy waves) and send the ultrasonic signals 25 down barrel 12 toward hub 18 and needle 16. The ultrasonic signals can travel through medication 20 along the length of barrel 12 and bounce or reflect off an end 27 of barrel 12 and travel back through medication 20 to plunger head 22. The reflected ultrasonic signals can be received and detected by transducer 24. The speed of sound in medication 20 may be a known value and thus a distance D can be calculated very accurately based on the time it takes for a ultrasonic signal to travel down and back from transducer 24. As plunger head 22 is moved down barrel 12 distance D will change and by knowing the diameter of barrel 12 then the volume of medication 20 dispensed may be calculated based on the change in distance D.

As shown in FIG. 5, in some embodiments, a porous membrane 29 may be placed within barrel 12 at end 27. Porous membrane 29 may be designed to allow medication 20 to pass through while providing a surface with good reflective properties for the ultrasonic signals 25 to reflect from. Utilizing porous membrane 29 may improve the accuracy of the reflective wave detection and thereby the distance and volume calculations. It is contemplated that other materials may be used besides a porous membrane. It is also contemplated that the geometry of barrel 12 at end 27 may dictate whether a porous membrane is needed. For example, in some embodiments the geometry of end 27 may be designed to produce the desired reflective properties avoiding the need to porous membrane 29.

In some embodiments, controller 26 may be configured to use the temperature of medication 20 to compensate for variations in the temperature that would affect the speed of sound within the medication, thus improving the accuracy of the distance and volume calculations.

In some embodiments, controller 26 may be attached to a printed circuit board and may include one or more processors, including for example, a central processing unit (CPU). The processors may include any suitable type of commercially available processor or may be a custom design. Controller 26 may include additional components, for example, non-volatile memory (e.g., a flash memory), volatile memory (e.g., a random access memory (RAM)), and other like components, configured to store information). Controller 26 may be a microcontroller that can be dynamically updated or include logic that is implemented in static hardware.

Controller 26 may be programmed with instructions to control the operation of transducer 24. Controller 26 may be programmed with instructions to calculate data representative of the volume of medication 20 dispensed. For example, in some embodiments, controller 26 may be programmed to detect and record the reflection times of the ultrasonic signals 25. Based on the reflection times, controller 26 may track and produce a time profile of the position of transducer 24 (i.e., plunger head 22). Based on the time profile of the position, controller 26 may be able to identify a first distance D1 or starting position (e.g., before medication 20 is dispensed), which may correspond with barrel 12 being filed and a second distance D2 or ending position (e.g., after medication 20 is dispensed), which may correspond with barrel 12 being empty. Controller 26 may then calculate the change in distance between D1 and D2 and based off of the change in distance may calculate the volume (i.e., amount or quantity) of medication 20 dispensed.

In some embodiments, medication 20 may include an active medication ingredient and a buffer solution. The concentration of the active medication ingredient may be known or programmed into controller 26 enabling the specific volume of the active medication ingredient to be calculated. In some embodiments, for example, the concentration of the active medication ingredient may be stored in the non-volatile memory of controller 26. In some embodiments, additional information regarding the medication 20 may also be stored, for example, ultrasonic velocity vs. temperature data.

Transducer 24 and/or controller 26 may be programmed to perform various forms of signal conditioning in order to detect the time of the reflected ultrasonic signals 25. The signal conditioning may include, for example, amplification, filters, and envelope detection. Transducer 24 and/or controller 26 may use the signal conditioning to determine for example, time to first rising edge or time to maximum reflective value in order to determine the reflection time.

Figure 6:
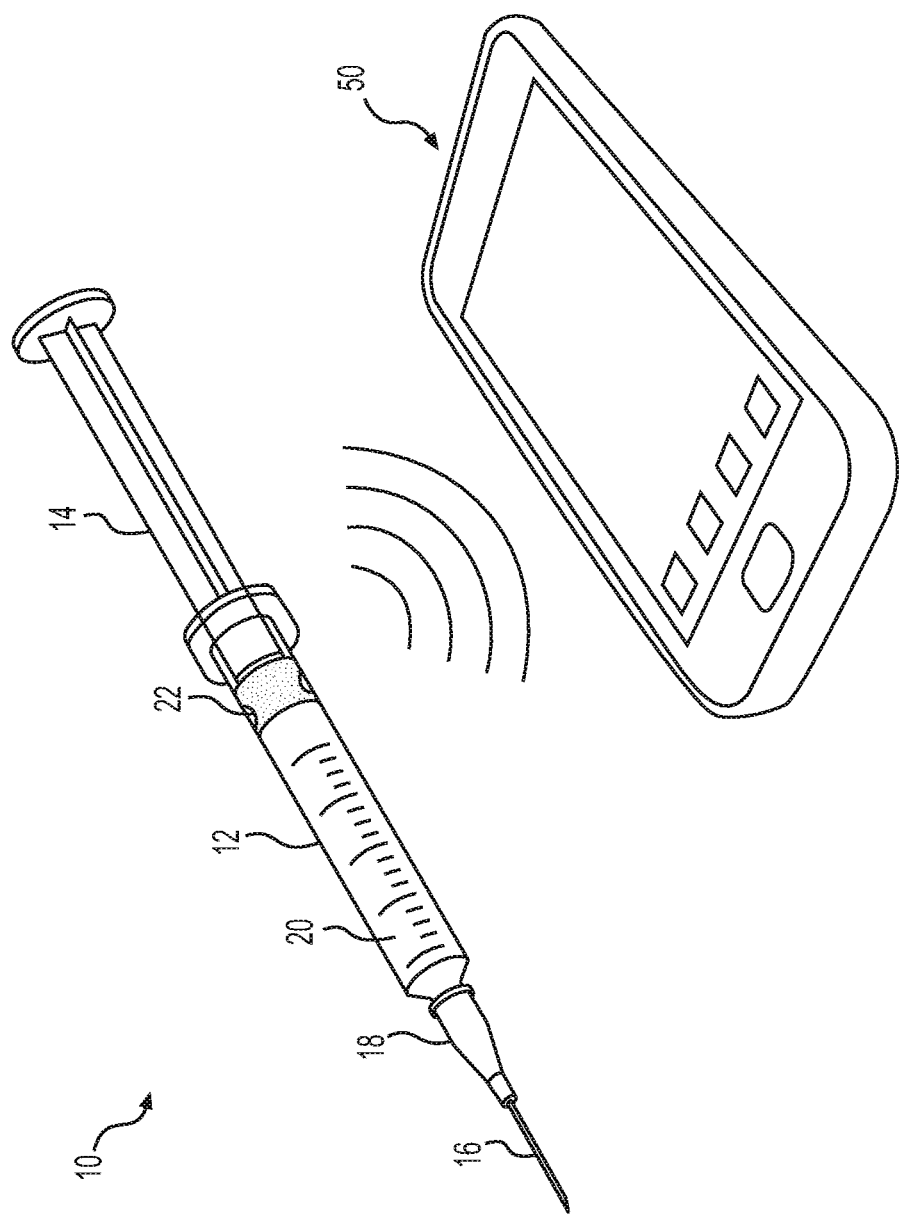
FIG. 6 is a perspective view of the medication injection device of FIG. 1 communicating with a remote device, according to an exemplary embodiment.

Plunger head 22 may transmit data (e.g., the amount of medication 20 dispensed and time and date it was dispensed) to a remote device (e.g., a smart phone, a glucose monitor, an insulin pump, or a computer) via one or more of the wireless communication methods. For example, as shown in FIG. 6, plunger head 22 may transmit data to a remote device 50, which may be a smart phone. Plunger head 22 may have a unique identifier so remote device 50 may be able to identify and process the information received properly. Plunger head 22 may transmit this information to remote device 50 immediately or shortly after the medication is administered or plunger head 22 may store the information until the remote device is paired and within range. The information may be stored, for example, in memory of controller 26. In some embodiments, plunger head 22 may wait to initiate transmitting of the information to remote device 50 until initiated by remote device 50. For example, a user may initiate information retrieval on remote device 50. In some embodiments, remote device 50 may transmit the information to a caregiver (e.g., a doctor) or upload the information to the cloud so it may be saved to the patient's medical history and may be accessed by the caregiver. The ability of a caregiver or a patient to access and review the dose history may improve treatment. For example, the ability of a caregiver to review a diabetic insulin injection history and continuous glucose measurement data may enable the caregiver to adjust the prescribed treatment to improve the therapeutic effect, for example, by better stabilizing the patient's glucose levels.

Figure 7:
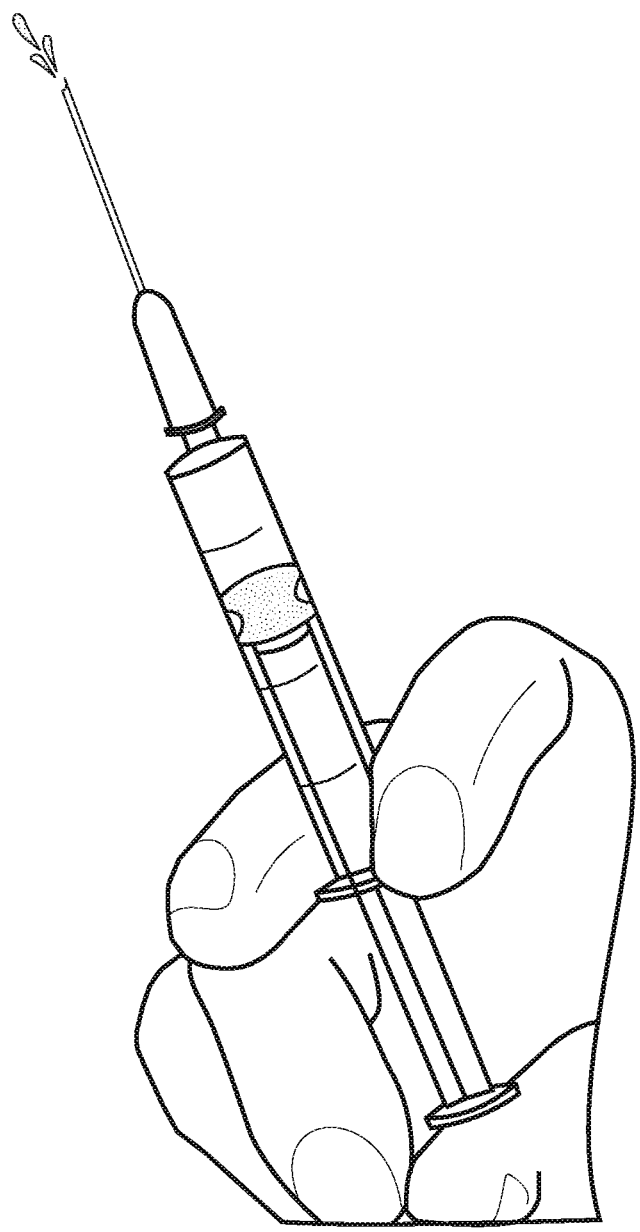
FIG. 7 is an illustration of an air shot being performed using a medication injection device, according to an exemplary embodiment.

Plunger head 22 and/or remote device 50 may be programmed to automatically differentiate a portion of the volume dispensed as part of an air shot versus the portion of volume injected into a patient. In other words, plunger head 22 and/or remote device may be programmed to detect and identify an air shot. An air shot may also be referred to as a prime shot or safety shot. An air shot is a common practice associated with medication injection devices (e.g., insulin pens and syringes) and is often a recommended step. An air shot may be defined as priming of the medication injection device by dispensing a small volume (e.g., 2 units) of medication 20 into the air prior to injection. For example, FIG. 7 shows an example of a user performing an air shot. The primary purposes of an air shot are to remove bubbles from the medication within the medication injection device, fill the needle, and clear any potential debris from the needle (e.g., when a needle is reused). It is usually recommended that one or more air shots should be performed until a steady stream is dispensed from the end of the needle.

Failure to differentiate and identify the volume disposed as part of an air shot from the total volume dispense could lead to more medication than was actually injected into a patient being recorded and this can lead to inaccurate medication injection records. By detecting an air shot, the volume of medication dispensed during the air shot can be subtracted from the total volume of medication 20 dispensed to determine the actual volume of medication 20 injected in a patient. In some embodiments, the volume of the air shot and the volume of the actual injection may be logged and recorded so a caregiver may monitor if recommended procedures (e.g., an air shot) are actually being followed and the frequency at which they are being followed.

An algorithm processing and analyzing the data collected, stored, and/or transmitted by plunger head 22 may be programmed to determine or identify an air shot based on one or more recognizable events (e.g., air shot events) that may be indicative of an air shot. In some embodiments, the algorithm may run locally on plunger head 22 (e.g., using controller 26). In some embodiments, the algorithm may run on remote device 50. In some embodiments, the algorithm may run elsewhere (e.g., in the cloud, remote server, or the like) and the data may be uploaded by remote device 50.

The algorithm may be programmed to identify an air shot based on one or more air shot events where the probability of accurate identification increases based on the number of air shot events utilized in combination. A variety of different air shot events may be detected and/or recognized and utilized by the algorithm as described below.

In some embodiments, for example, one air shot event the algorithm may use to identify an air shot may be an air shot volume event. An air shot volume event may be when a volume of medication is dispensed (e.g., 2 units) that is indicative of an air shot (e.g., air shot volume). For example, if two fluid dispensing events occur in a series, a controller may determine that the first fluid dispensing event is the air shot event if the first quantity of the fluid dispensed is smaller than the second quantity of the fluid dispensed. In some embodiments, an air shot volume event may be identified by controller 26 using the reflection times of the ultrasonic signals 25. For example, based on the reflection times of the ultrasonic signals 25 a change in the position of plunger head 22 and the dispensed volume may be calculated. When there is a volume dispensed in isolation, which corresponds to an air shot volume, controller 26 may identify this as an air shot volume event. Often, manufacturers of medical injection devices standardize their injection procedures based on industry norms and commonly the procedures instruct the patients to perform a 2-unit air shot before each injection. It is contemplated that the volume programmed to be indicative of an air shot may be adjusted if industry norms changes or other volumes of air shot may be utilized. In addition, the algorithm may utilize a volume range that may extend above or below 2 units (e.g., plus or minus 5%, 10%, 20%, 25%, or more) in order compensate for potential inaccuracy in a patient's operation or inaccuracy in a medication injection device.

Another air shot event the algorithm/controller may use to identify and air shot may be when a pattern of activity (e.g., a sequence of dispensed volumes) is indicative of an air shot. This type of air shot event may be referred to herein as an air shot pattern event. For example, often there may be long periods of inactivity (i.e., no dispensing) followed by a dispensing of a small dose (e.g., 2 units), quickly followed by dispensing of another dose, and then another long period of inactivity. The long period of inactivity typically corresponds to the time in between injections. The first small dose immediately following the inactivity is typically the air shot, and then the second dose is the actual injection. Thus, the algorithm may be programmed to detect when there is a long (or threshold) period of inactivity (e.g., 5 min, 10 min, or more), a small dispensing of fluid, a short gap (e.g., about 5 seconds, about 4 seconds, about 3 seconds, about 2 seconds), and a second volume of medication being dispensed. The algorithm may identify the first volume as an air shot and the second volume as an injection. In other words, a first volume of medication dispensed after a period of inactivity may be recognized as an air shot. This air shot event may be referred to herein as an air shot pattern event.

In situations where there may be more than two dispensed volumes, for example, a first volume, a second volume, and a third volume, the algorithm may be programmed to recognize the first two volumes as air shot, which may be the case if a second air shot was needed to achieve a steady unimpeded stream from the needle.

Another air shot event the algorithm may use to identify an air shot may be when a rate of pressure change of medication 20 within barrel 12 is indicative of an air shot. This type of air shot event may be referred to herein as an air shot pressure event. In order to measure the pressure change, in some embodiments, transducer 24 may be configured to operate as a piezoelectric element, which can output a pressure signal to controller 26 indicative of the present pressure within barrel 12. In this embodiment transducer 24 is acting as a dosage tracking system. Thus, data representative of pressure over time may be collected by controller 26 when a volume is dispensed from barrel 12. The pressure over time data may be used to calculate a rate of pressure change. It is generally expected that a faster rate of pressure change will correspond with an air shot, because for an air shot, medication 20 is simply being shot in the air against no back pressure, for example, as shown in FIG. 7. In contrast, when medication 20 is injected into a patient there is a back pressure caused by the tissue, thus the rate of pressure change during an injection will be slower than that during an air shot. Based on this expectation, controller 26 may be programmed to identify a dispensing event as an air shot pressure event if the rate of pressure change is above a pressure change threshold, or if a first rate of pressure change is greater than a second rate of pressure change in a series of dispensing events.

Another air shot event the algorithm may use to identify an air shot may be when plunger head 22 moves at a velocity indicative of an air shot. This type of air shot event may be referred to herein as an air shot velocity event. For example, a velocity (V) of plunger head 22 during medication dispensing may be calculated using equation (1) shown below, based on the change in distance (d) over time (t).

$$V = \Delta d/t \qquad \text{Equation (1)}$$

It is generally expected that the velocity of plunger head 22 will be greater during an air shot because of the absence of back pressure compared to an injection. Based on this expectation, controller 26 may be programmed to identify a dispensing event as an air shot velocity event if the velocity during the dispensing event is above a velocity threshold, or if the velocity of dispensing first dispensing event in a series of dispensing events is greater than a second dispensing events. The velocity may be indirectly measured with a dosage tracking system (in this embodiment the transducer measuring the position) and output to the controller.

In some embodiments, the algorithm may also be programmed to incorporate and recognize an air shot based on the orientation or the movement of the medical injection device or plunger head 22. For example, in some embodiments plunger head 22 may include an accelerometer (or other orientation tracker) that controller 26 may utilize to determine and track orientation or movement of plunger head 22 and syringe 10. For example, the accelerometer output may be used to identify when the syringe 10 is positioned in a generally vertical orientation (e.g., dispensing end of the medication injection device is pointing upwards), as shown in FIG. 7, which is commonly the orientation when performing an air shot because it facilitates the bubbles moving to the top and getting removed. In other words the orientation tracker may calculate an orientation of the medication injection device, and output an indication of the orientation in the data sent to the controller. This type of air shot event may be referred to herein as an air shot orientation event.

It is also common to tap or strike the side of barrel 12 before performing an air shot to dislodge bubbles and the tapping or striking motion of the barrel may be detected by the accelerometer and recognized as a bubble dislodge event that is likely to be followed within a threshold period of time by a volume of medication dispensed as an air shot. This type of air shot event may be referred to herein as an air shot bubble dislodge event. For some injections, mixing of the medication is also performed prior to performing an air shot and injection. Often mixing of the medication is done by rolling the syringe back and forth on a table or in between a person's hands. The rolling of the syringe back and forth will likely result in a unique easily identifiable series of outputs from the accelerometer, which the algorithm may utilize to recognize that it is likely that an air shot will be performed shortly after this event within a threshold period of time. This type of air shot event may be referred to herein as an air shot mixing event. Thus, the first fluid dispensing event after a bubble dislodge event (e.g., the characteristic acceleration of tapping/striking the medication injection device) or after a mixing event (e.g., the characteristic acceleration of rolling the syringe) can likely be characterized as an air shot event.

In some embodiments, the algorithm may be programmed to recognize an air shot based on a single air shot event. For example, in some embodiments, the algorithm may be programmed to identify an air shot based an air shot volume. However, utilizing just a single type of air shot event (e.g., based on volume alone) could lead to misidentification of air shots. For example, if the algorithm is programmed to identify a 2-unit dispensed volume (i.e., an air shot volume event) as an air shot it may misidentify a 2-unit injection as an air shot. The other types of air shot events may be utilized in isolation to identify an air shot and in some cases may provide more reliable accuracy. For example, the algorithm may be programmed to recognize an air shot based an air shot pattern event, air shot pressure event, air shot velocity event, air shot orientation event, air shot bubble dislodge event, or air shot mixing event.

In some embodiments, the algorithm may utilize two or more type of the air shot events described herein to recognize an air shot. When the algorithm utilizes multiple events to recognize an air shot it can limit or prevent misidentification of an air shot or failure to identify an air shot. In other words, the more events the algorithm utilizes and detects may increase the probability of accurate air shot detection. The algorithm may utilize any number and combination of the events described herein. For example, in some embodiments the algorithm may be programmed to utilize an air shot pattern event in combination with an air shot volume event. In other embodiments, the algorithm may also incorporate in an air shot pressure event and/or an air shot velocity event to further increase the probability of accurate air shot identification. These combinations of events do not rely on any output from the accelerometer so these combinations of events may be utilized with a plunger head 22 that does not include an optional accelerometer. In contrast, an embodiment of plunger head 22 having an accelerometer may utilize these combinations of events in addition to an air shot orientation event, air shot bubble dislodge event, and an air shot mixing event.

In some embodiments, the algorithm may be programmed to calculate and record an accuracy probability of each recognized air shot based on the number of events and which events were utilized in the determination. In some embodiments, the algorithm may adjust over time which type of events it uses to identify an air shot based on a patient's prior injection routine or behavior. In other words, the algorithm may evaluate prior injection behavior and based on that prior behavior may select the air shot events that will produce the highest likelihood of accurate air shot identification.

It is contemplated that a variety of strategies of programming may be utilized for the algorithm. For example, in some embodiments the algorithm may be programmed to identify an air shot when, for example, two, three, or more of the events are all detected. In other embodiments, the algorithm may be programmed to identify an air shot when at least a portion of the events are detected. For example, the algorithm may be programmed to identify an air shot when two or more out of the total number of events the algorithm is utilizing are detected. Which two or more are detected may vary from air shot to air shot. In some embodiments, the algorithm may be programmed to always require the detection of at one of the events before identifying an air shot.

Now referring back to FIG. 2, in some embodiments, plunger head 22 may also include a crystal oscillator 32 configured to keep a real time clock (RTC) so that the date and time of each injection may be accurately recorded and stored in memory of controller 26. Crystal oscillator may be, for example, a 32 KHZ crystal oscillator. In some embodiments, controller 26 may include an internal oscillator (e.g., RC oscillator), which may be calibrated using crystal oscillator 32. The internal RC oscillator may be, for example, a 10 MHZ RC oscillator. Internal RC oscillator may provide sufficient time accuracy to measure the position (e.g., distance D) of plunger head 22 to within, for example, about 150 microns. In some embodiments, transducer 24 may be used as an oscillator or as a calibrator for the internal RC oscillator. In some embodiments, the frequency of the RC oscillator may be up-converted on controller 26 to a higher frequency. For example, the RC oscillator may be used to drive a higher-frequency phase-locked loop.

In some embodiments, plunger head 22 may be designed to back-interpolate the time of each injection enabling crystal oscillator 32 to be eliminated. In order to maintain the RTC, crystal oscillator 32 may consume a significant amount of power, thus eliminating the crystal oscillator 32 can save a significant amount of power as well as save space.

Plunger head 22 may back-interpolate the time of each injection by relying on the real time clock of the remote device. The method of back-interpolating may start with plunger head 22 taking and logging a series of data samples (e.g., plunger head 22 positions). Plunger head 22 may be programmed to take and log the data samples at an approximately regular interval. The data samples, may be stored, for example in a memory of controller 26 in the order measured. The data samples may be logged and stored into memory with other data values (e.g., calculated injection volume, temperature, etc.). The collection of logged data samples may be transferred/transmitted (e.g., uploaded) to a remote device, which will receive the data samples in the same order. The remote device may rely on the approximately regular interval of the data sample logging to back-interpolate from the actual time at time of transfer, as determined by the RTC of the remote device. By back-interpolating the approximate time of each data sample logged may be determined. For example, if there were six samples transferred to the remote device and they were known to have been captured at about 60 minute intervals then the remote device may determine the time of each of the six samples were logged working backwards from the time of data transfer. However, this example produces about a 60 minute uncertainty in the calculated time of the data sample points because the time of transfer may not be synchronized with the time of data sample logging. However, plunger head 22 may be programmed to log data samples at a faster frequency to reduce the uncertainty or increase the accuracy. For example, data samples may be logged every 30 minutes, 15 minutes, 10 minutes, 5 minutes, 1 minute, or less than 1 minute.

The approximately regular interval may be determined or maintained by a less accurate, less power consuming, smaller timing device (e.g., an oscillator). It is noted that the reduce accuracy of the timing device may result in the approximately regular interval drifting due to a variety of factors, for example, temperature, voltage, or factory-determined offsets. However, in some embodiments, plunger head 22 may store the factory determined offsets and be programmed with instructions to measure and log the temperature and/or voltage. Controller 26 may be programmed with instructions to use the factory determined offsets and the logged temperatures and voltages to generate a model to correct drift (i.e., change in interval) between the approximately regular intervals caused by variability in the temperature and the voltage. This same method may also be used in other embodiments to correct drift even in a more accurate time tracking system (e.g., a quartz referenced system).

Although the above described back-interpolation and drift correction method is described in reference to plunger head 22, it is contemplated that this method could be used in other sensor or sampling systems to provide timestamps of useful accuracy for a sequence of sensor samples that do not contain an accurate time reference. This method provides cost, power, and space savings while providing an accurate time reference for a sensor system.

Antenna or transceiver 30 may be used to communicate with a variety of remote devices (e.g., smart phones, glucose monitors, insulin pumps, computers, etc.). Plunger head 22 may transmit the information via any suitable wireless communication method. For example, in some embodiments, plunger head 22 may utilize radio data transmission, BLUETOOTH or BLUETOOTH LOW ENERGY (BLE), near field communication (NFC), infrared data transmission or other suitable method. In some embodiments, information may also be wirelessly transmitted from a remote device to plunger head 22 via antenna 30. For example, the date and time may be set by writing to controller 26 via the wireless communication.

In some embodiments, plunger head 22 may also include a force sensor 34. Force sensor 34 may be configured to detect when a force is applied to plunger head 22 via plunger 14. Force sensor 34 may be, for example, a simple spring-loaded switch that is molded into the plunger head 22. In some embodiments, transducer 24 may be configured to function as a force sensor thereby eliminating the need for a separate force sensor 34. For example, transducer 24 may have a piezoelectric element that may detect the dynamic changes in pressure when a user depresses plunger 14.

Power source 28 may be any suitable power source. For example, power source 28 may be a battery, a capacitor, or the like. In some embodiments, power source 28 may be rechargeable via wireless energy transmission, for example, inductive coupling, resonant inductive coupling, radio frequency (RF) link, or the like. In some embodiments, power source 28 may be a non-rechargeable battery that is configured to last the storage and operational life of plunger head 22, for which the combined storage and operational life may be about 1 year, about 2 years, about 3 years, or more. For example, in some embodiments, power source 28 may be a watch battery. In some embodiments, where plunger head 22 is a passive device as described herein, power source 28 may be eliminated.

It is common for goods, including medical injection devices, to have a long storage life between the time of manufacture and time of use/sale. Products that include embedded electronics, in particular a battery, it can be a challenge to conserve battery power while the products are in storage. Some products have no on/off switch, buttons, or removable/rechargeable batteries, so the traditional approach of disconnecting or turning off the device while in storage may not be feasible. Also, certain products (e.g., medical injection devices) that include perishable goods (e.g., medication) it may be advantageous to have the product monitor the storage environment (e.g., temperature, light, etc.) and log or store this data and this can't be done if the battery is disconnected.

To address this challenge, plunger head 22 may be designed to enter a low-power sleep mode while in storage. Plunger head 22 may be programmed to enter low-power sleep mode as part of the manufacturing and testing process for plunger head 22 or the medication injection device. When in low-power sleep mode the rate of power consumption may be a fraction of the rate of power consumption for normal operation. While in low-power sleep mode, controller 26 may be programmed with instructions to periodically wake up to measure the temperature. Controller 26 may also log the temperature to create a temperature history. Alternatively, in some embodiments controller 26 may be programmed to log the temperature only when there is a change in temperature, thus saving on data storage. The efficacy of some medications is affected by temperature. For example, insulin is sensitive to hot and cold temperatures. Plunger head 22 thus may monitor the temperature medication 20 through storage and up through use to ensure it stays within an acceptable range. If the temperature of the medication 20 goes outside the acceptable range then plunger head 22 may be configured to send an alert. The type of alert may vary. In some embodiments, plunger head 22 may include a display (not shown in FIG. 2) and the alert may be a flashing light or a visual indicator. In some embodiments, plunger head 22 may include a speaker and the alert may be auditory, for example, a beeping sound. In some embodiments, the alert may be transmitted to a remote device and the remote device may display a visual alert and/or play an auditory alert.

In some embodiments, plunger head 22 may also be designed to utilize the temperature measurement to transition between modes. For example, a medication injection device that includes plunger head 22 and medication 20 may often be stored at a lower temperature (e.g., below a normal room temperature of about 20 to about 22 degrees Celsius). Subsequently, prior to use, often the temperature will be the medication device, including plunger head 22 and in particular medication 20 will be raised to room temperature because injection of cold fluids can be painful. Thus, usually there will be a transition from a lower temperature to a higher temperature shortly before use thereby triggering a change in the mode of plunger head 22.

As described above, in lower power sleep mode plunger head 22 can periodically measure the temperature, thus controller 26 may be programmed to detect the temperature change that is expect prior to use and when detected controller 26 may be programmed to transition plunger head 22 from low-power sleep mode into an initialization mode. Controller 26 may be programmed to pair with a remote device while in the initialization mode. After a successful pairing, controller 26 may be programmed to transition plunger head 22 to an operational mode and start sending and receiving ultrasonic waves and measuring the position of transducer 24. In some embodiments, controller 26 may be programmed to reenter the low-power sleep mode if it is unable pair with a remote device within a certain period of time (e.g., if no remote device is present). Controller 26 may also be programmed to reenter the low-power sleep mode after a period of inactivity (e.g., no measurable change in transducer 24 position after a programmed period of time). Controller 26 may also be programmed to reenter the low-power sleep mode if a subsequent temperature change (e.g., a decrease in temperature from normal room temperature) is detected. Controller 26 may be programmed to transition directly from the low-power sleep mode back to the operational mode if a successful pairing with a remote device has already occurred.

In some embodiments, plunger head 22 may also be configured to detect air bubbles in medication 20. Air bubbles if injected can be deadly so detection of air bubbles is advantageous. In order to detect air bubbles, transducer 24 of plunger head 22 may be configured to detect small ultrasonic echoes created by the reflection of the ultrasonic waves off the air bubbles in addition to the main echo caused by the end of barrel 12. Plunger head 22 may be configured to transmit an alert if air bubbles are detected. The alert may be communicated in the same ways as the temperature alert described above.

In some embodiments, plunger head 22 may also be configured to differentiate, verify, and/or identify medication 20 contained in syringe 10. For example, when barrel 12 is loaded with medication 20, plunger 14 and plunger head 22 may be pulled all the way back to its stopping point and the distance from plunger head 22 to end 27 of barrel 12 may be known enabling controller 26 to solve for the speed of sound of the fluid, which depends on temperature and density. The temperature may be measured by temperature sensor 36 so the density may be determined and based on the density the amount of solids dissolved in the fluid may also be determined. In addition, the viscosity of the medication 20 may be measured based on the amplitude of the reflected ultrasonic signals 25 because more viscous fluids dissipate more energy. In some embodiments, plunger head 22 may also include electrodes 38 connected to controller 26 configured to measure the conductivity of medication 20. In some embodiments, the electrodes 38 may protrude out from the surface of plunger head 22 into barrel 12 where the electrodes 38 may contact medication 20. With the density, conductivity, and viscosity of medication 20 determined, controller 26 may have a sufficient number of properties to profile medication 20. In some embodiments, the profiling may be configured to differentiate medication 20 in order to determine if it from a prescribed class of medication. In some embodiments, the profiling may be configured to verify that medication 20 is the same as the medication that is prescribed for the patient. In some embodiments, the profiling may be configured to identify the medication 20.

According to an exemplary embodiment, plunger head 22 as described herein may be combined with a syringe that has been modified to include a piezo linear motor. The piezo linear motor may be incorporated into the wall of the barrel of the syringe and a piezo element may be incorporated into plunger head 22. The piezo linear motor may be configured to drive or "walk" the plunger head 22 down the barrel of the syringe by driving the piezo element, thereby forcing the medication from the syringe. This embodiment may enable the piezo linear motor to control medication dispensing while plunger head 22 may simultaneously track the amount of medication being dispensed. In some embodiments, plunger head 22 may control the piezo linear motor or plunger head 22 can communication with a remote device that can control the piezo linear motor such that it dispenses a set amount of medication.

Figure 8:
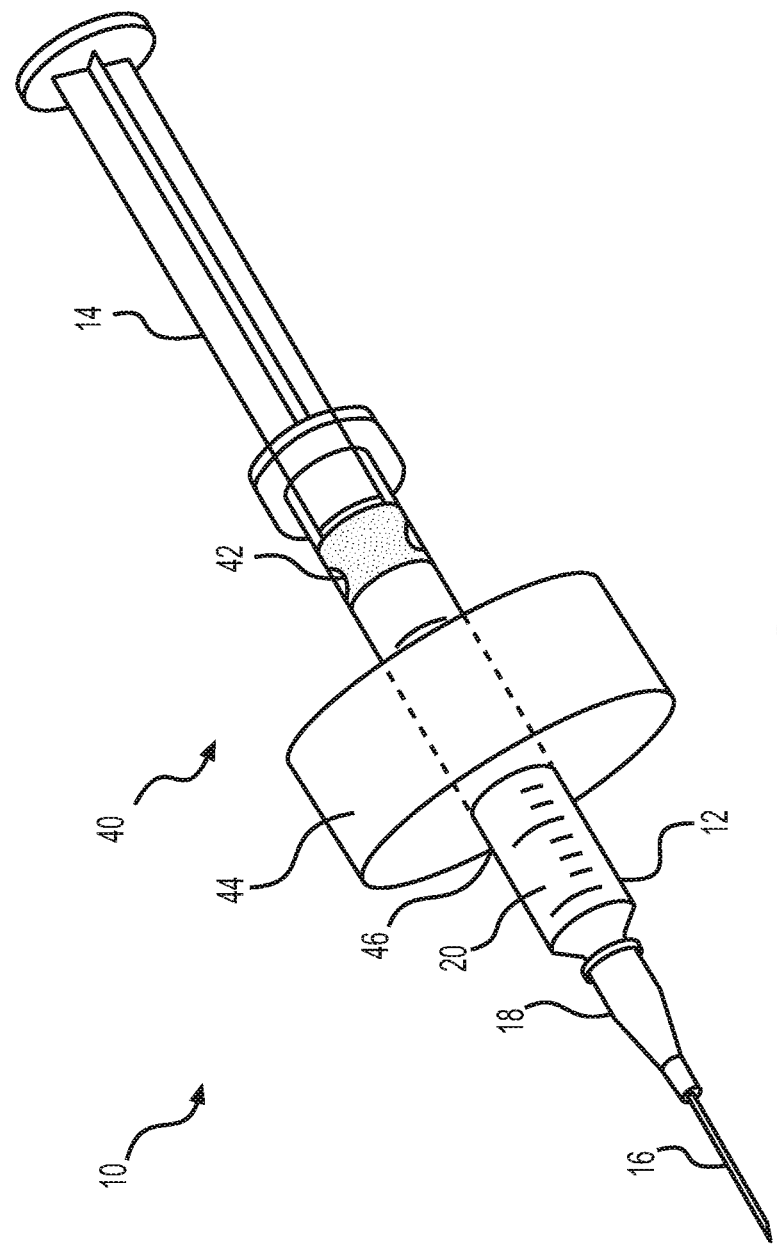
FIG. 8 is a perspective view of a medication injection device, which includes a plunger head and a cuff, according to an exemplary embodiment.

FIG. 8 shows a smart syringe system 40, according to another exemplary embodiment. System 40 may be designed for use with a standard disposable syringe 10 or other medication injection devices. Similar to plunger head 22, smart syringe system 40 may be configured to measure and register the quantity of medication 20 administered and the date and time of administration. Smart syringe system 40 may include a smart or intelligent plunger head 42, similar to plunger head 22, and a cuff 44. In some embodiments, plunger head 42 may be designed to be disposable after a single use while cuff 44 is reusable. Embodiments of plunger head 42 designed to be disposable after a single use may houses only the minimum number of components to carry out its function while any optional or ancillary components may be housed in cuff 44 to minimize manufacturing cost of plunger head 42. The manufacturing cost of plunger head 42 may also be minimized by using lower cost components (e.g., transducers, antennas, and controllers) and materials (e.g., rubbers, polymers, plastics) that are less robust and durable, and instead may be designed for shorter operational life spans.

Plunger head 42 may be designed to be supplied with or installed into a disposable syringe 10 and after administering a dose of medication 20, syringe 10 along with plunger head 42 may be disposed of or recycled. In contrast, cuff 44 may be designed to be reused numerous times. For example, a disposable syringe 10 may be inserted through cuff 44 and after medication 20 is administered; cuff 44 may be removed from the used syringe 10 and be saved for later use.

In some embodiments, both plunger head 42 and cuff 44 may be reusable. For example, after medication 20 is administered by syringe 10, both plunger head 42 and cuff 44 may be removed and saved for later use.

Plunger head 42 and cuff 44 can come in different sizes so they may be used with any size syringe. For example, plunger head 42 may be sized to fit within the barrel 12 of any size syringe 10 while cuff 44 may be configured to have a passage 46 configured to receive any size barrel 12 of syringe 10.

Plunger head 42 and cuff 44 (i.e., the smart syringe system 40) in combination may be configured to have some or all of the same components (e.g., a transducer 24, a controller 26, a power source 28, an antenna 30, crystal oscillator 32, force sensor 34, and a temperature sensor 36) as plunger head 22 and perform at least all the same operations as plunger head 22. Some of the components may be housed in plunger head 42 while some of the components may be housed in cuff 44. To reduce the manufacturing cost of plunger head 42, as described above, plunger head 42 may be designed to house the minimum number of components to carry out its functions. For example, system 40 may be configured such that all the components that can be housed in cuff 44 are, rather than plunger head 42. In some embodiments, such components may include a form of memory for data storage.

According to an exemplary embodiment, plunger head 42 may include the transducer 24, antenna 30, and a controller 26 while cuff 44 may also include a separate controller, a power source, and a separate antenna. To reduce complexity, plunger head 42 may be passive (e.g., battery-free) and configured to be controlled and powered by cuff 44 via wireless energy transmission. Cuff 44 may also be configured to communicate with a remote device (e.g., a smart phone, a glucose sensor, an insulin pump, or a computer) thereby enabling the volume of medication and the time and date of administering to be uploaded to another device or the cloud.

In some embodiments, cuff 44 may include a display. Cuff 44 may be configured to display any alerts (e.g., high temperature or improper medication) to the user. Cuff 44 may also display the volume, date, and time after medication has been dispensed. The display may also be configured to allow user input (e.g., touch screen). For example, the user may program in the date, the time, the type of medication or other information.

Figure 9:
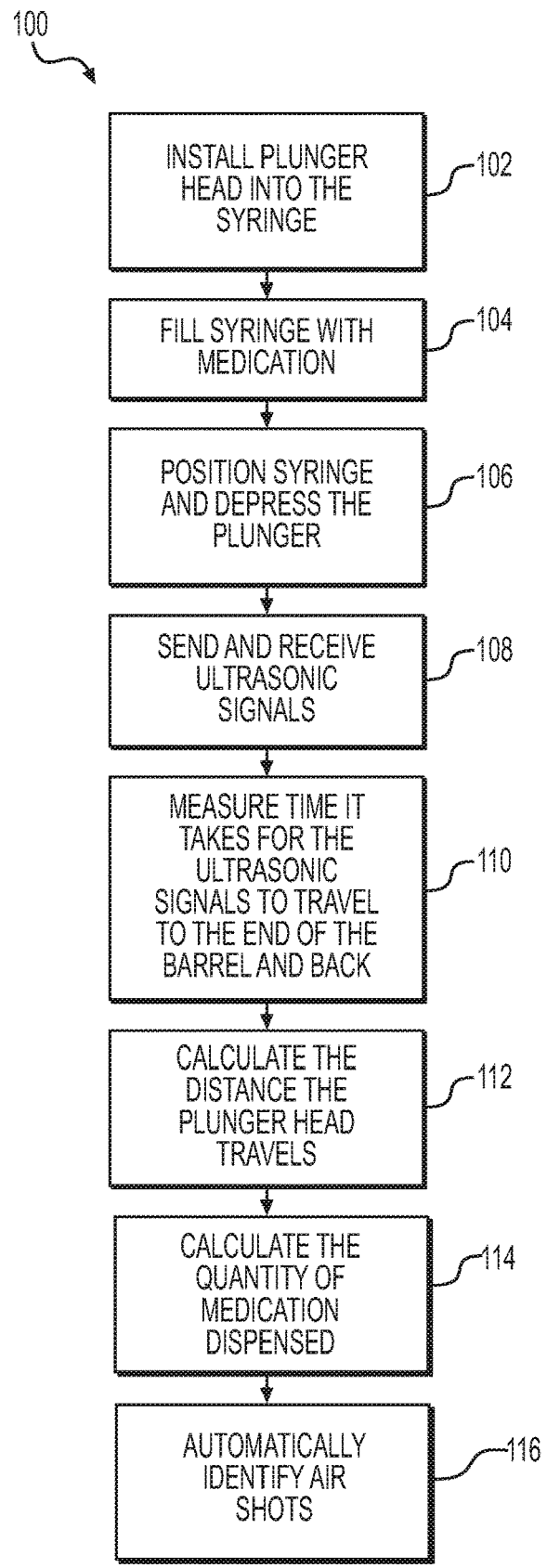
FIG. 9 is a flow chart illustrating a method of tracking administering of medication by a medication injection device, according to an exemplary embodiment.

Plunger head 22 and system 40 described herein may be utilized for a variety of methods for tracking administering of a medication to a patient delivered by syringe. Various methods of utilizing plunger head 22 and system 40 will now be explained with reference to FIG. 9. In some embodiments, the methods as described herein may be performed by a caregiver (e.g., a doctor or nurse) in a hospital or other inpatient setting. In some embodiments, the methods as described herein may be performed by a caregiver (e.g., a doctor, nurse, or parent) at home or outside a hospital. In some embodiments, the methods as described herein may be performed by the patient. It is contemplated that the methods described herein may be performed in other settings by other individuals.

Plunger head 22 may be utilized for a method 100 of tracking administering of a medication to a patient delivered by a medication injection device (e.g., a syringe), according to an exemplary embodiment. In some embodiments, at step 102, method 100 may begin by installing plunger head 22 into barrel 12 of syringe 10 (e.g., a disposable syringe). In some embodiments, syringe 10 may be supplied with plunger head 22 already installed. For embodiments corresponding to other medication injection devices (e.g., insulin pen), plunger head 22 may be installed as part of the original manufacturing process, which may also include loading of medication 20 (e.g., insulin).

Optionally, at step 104, the barrel 12 of the syringe may be filled with the medication 20. This step may be eliminated for embodiments were the medication 20 comes prefilled. The barrel 12 may be completely filled or only partially with medication 20.

At step 106, the syringe may then be positioned for delivery. For example, the needle may be inserted into the skin of the patient or into a drug delivery port connected to the patient. Once in position, the plunger 14 of the syringe 10 may be depressed, which forces plunger head 22 down the barrel 12 and forces the medication 20 out the needle 16. Optionally, prior to step 106, method 100 may also include performing an air shot.

In some embodiments, the initial position of plunger head 22 (e.g., the distance between plunger head 22 and end 27) may be known by plunger head 22. For example, syringe 10 may be full and plunger head 22 may know the distance between plunger head 22 and end 27 when filled. In some embodiments, if syringe 10 is used multiple times to deliver a medication 20, the previous position of plunger head 22 may be known from the last measurement stored. In some embodiments, the initial position of plunger head 22 may be measured using plunger head 22 prior to any medication 20 being delivered, as described below.

Prior to and while plunger 14 is being depressed, plunger head 22 may send and receive ultrasonic signals 25 via transducer 24, at step 108. Plunger head 22 may send and receive ultrasonic signals 25 the duration of the time the plunger is being depressed. Plunger head 22 may measure a time it takes for each of the ultrasonic signals to travel through the medication to an end of the barrel and return to the transducer, at step 110. In some embodiments, at least a portion of the ultrasonic signals 25 may be sent and received before any medication 20 is dispensed enabling the initial position of plunger head 22 and initial volume of medication 20 to be calculated.

As described herein, at step 112, plunger head 22 may calculate the position of plunger head 22 and a distance plunger head 22 travels over the course of dispensing medication 20. At step 114, the quantity of medication 20 dispensed may be calculated based on the calculated distance plunger head 22 traveled. At step 116, method 100 may include automatically identifying an air shot, as described herein. If an air shot is identified then the volume medication dispensed as part of the air shot may be subtracted from the total volume dispensed in order to determine the actual volume of medication 20 injected. As described herein, an algorithm may be utilized that analyzes the data collected to recognize one or more events indicative of an air shot.

For some embodiments of method 100, the calculation of the quantity of medication dispensed may be performed by remote device 50 (e.g., a smart phone, a glucose sensor, an insulin pump, or a computer). In some embodiments, method 100 may also include transmitting the quantity of the medication dispensed and the time and date the quantity was dispensed to a remote device. In some embodiments, method 100 may also include uploading the quantity of the medication dispensed and the time and date the quantity was dispensed to the cloud. In some embodiments, method 100 may also include sending the quantity of the medication dispensed and the time and date the quantity was dispensed to a caregiver.

For some embodiments, method 100 may also include logging a plurality of data samples (e.g., position of plunger head 22) at an approximately regular interval and then back-interpolating the time corresponding to each data sample logged to determine the approximate time the quantity of medication 20 was disposed using the RTC maintained by the remote device as a reference time.

Although method 100 is described with reference to plunger head 22, it may also be performed by system 40, as described herein.

Figure 10:
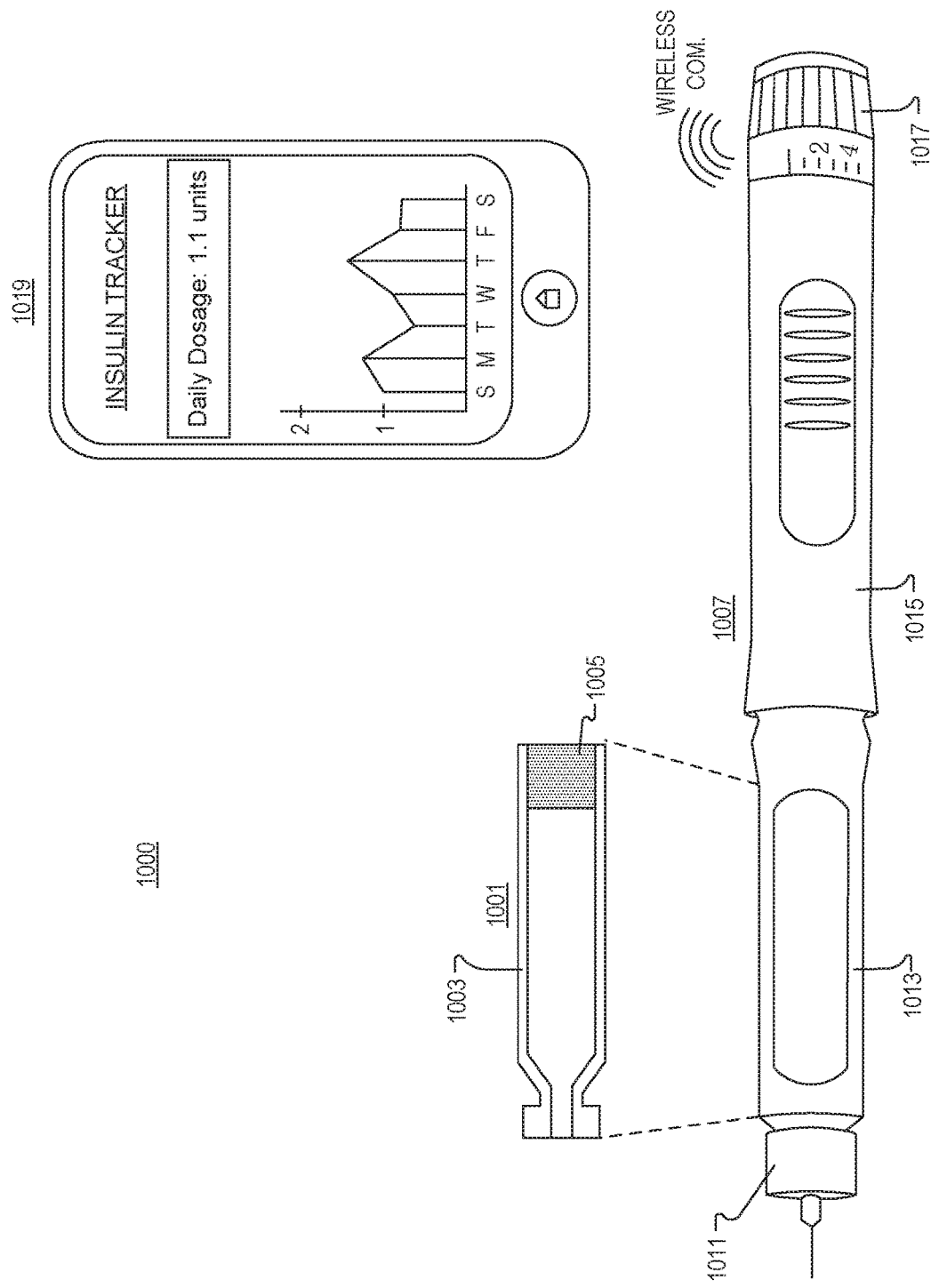
FIG. 10 is an illustration of an injection pen system to detect air shots, according to an exemplary embodiment.

FIG. 10 is an illustration of an injection pen system 1000 to detect air shots, according to an exemplary embodiment. Pen system 1000 includes drug cartridge 1001, injection pen 1007, and processing device 1019 (e.g., a smart phone). Similar to the embodiments described above, before an injection, pen system 1000 may perform an air shot.

Drug cartridge 1001 includes cartridge body 1003 (i.e., a "barrel"), and plunger head 1005. In the depicted embodiment, plunger head 1005 starts near the rear of drug cartridge 1001 and is pushed forward in drug cartridge 1001 (with a plunger in pen 1007) to expel medication/fluid from the narrow end of drug cartridge 1001. Plunger head 1005 may come pre-installed in drug cartridge 1001, or may be swapped in by a user. Similar to other embodiments, plunger head 1005 may include any of the electronics described above to send and receive ultrasonic signals, measure pressure, measure velocity, etc.

Injection pen 1007 is a hand-held device and includes needle 1011, chamber 1013 (to hold drug cartridge 1001), body 1015 (including a drug dispensing actuator—"plunger"—to push in plunger head 1005 and extract fluid from drug cartridge 1001), and a drug delivery control switch 1017 (twist the switch to "click" control the dosage). However, as one of ordinary skill in the art will appreciate, injection pen 1007 can take other configurations and have other components. In one embodiment, a dosage measurement system is disposed within pen 1007, to measure one or more of the quantity of fluid dispensed, pressure in cartridge 1001, number of injection events, fluid velocity during an injection, etc. In some embodiments, the dosage measurement system may include an accelerometer to measure the orientation of injection pen 1007, and if a user has tapped/rolled the pen to remove bubbles. The dosage measurement system in injection pen body 1015 may also include mechanical devices to measure the movement of the plunger (e.g., an encoder or pawl/cogwheel) in injection pen body 1015 in order to determine a volume of fluid dispensed. Injection pen body 1015 may include any of the hardware and logic described above in connection with the syringe embodiments, in accordance with the teachings of the present disclosure. These components may be disposed anywhere in injection pen 1000.

Processing device 1019 (e.g., a smartphone, tablet, general purpose computer, distributed system, servers connect to the internet, or the like) may be coupled to receive data from injection pen 1007 or drug cartridge 1001 to further store/analyze the data. Processing device 1019 may receive the data through any wireless transmission method such as Bluetooth, RFID or the like. In the depicted embodiment, processing device 1019 is a smartphone, and the smartphone has an application running recording how much insulin has been spent from injection pen 1007. Moreover the application is plotting how much insulin has been injected by the user over the past week.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A medication injection device, comprising:
 a plunger configured to fit, at least partially, within a barrel to dispense a fluid from the barrel;
 a dosage tracking system configured to output data indicative of an amount the fluid dispensed, wherein the dosage tracking system is disposed in a plunger head of the medication injection device and includes an ultrasonic transducer oriented to emit ultrasonic signals through the fluid along a length of the barrel and to receive reflected ultrasonic signals when the plunger is positioned within the barrel, and wherein the data is indicative of a time of flight of the ultrasonic signals; and
 a controller disposed within the medication injection device and coupled to the dosage tracking system to receive the data output from the dosage tracking system, wherein the controller includes logic that when executed by the controller causes the controller to perform operations including:
  determining, based on the data, whether an air shot event occurred while dispensing the fluid, including:
   measuring a distance traveled by the plunger head based upon the time of flight of the ultrasonic signals; and
   determining that the air shot event occurred when the distance traveled by the plunger head is below a threshold distance.

2. The medication injection device of claim 1, wherein the air shot event includes a fluid dispensing event where the fluid is deemed not to have been injected into a body.

3. The medication injection device of claim 1, wherein the dosage tracking system further includes an orientation tracker to calculate an orientation of the medication injection device and to output an indication of the orientation in the data, and wherein determining, based on the data, whether the air shot event occurred while dispensing the fluid further comprises:
 determining that the air shot event occurred when a dispensing end of the medication injection device is pointing upwards while dispensing the fluid.

4. The medication injection device of claim 1, wherein determining, based on the data, whether the air shot event occurred while dispensing the fluid further comprises:
 measuring quantities of the fluid dispensed during a sequence of fluid dispensing events including a first fluid dispensing event and a second fluid dispensing event, the first fluid dispensing event occurring prior the second fluid dispensing event, wherein the quantities include a first quantity of the fluid from the first fluid dispensing event and a second quantity of the fluid from the second fluid dispensing event;
 comparing the first quantity of the first fluid dispensing event to the second quantity of the second fluid dispensing event; and
 determining that the first fluid dispensing event is an occurrence of the air shot event when the first quantity of the fluid is smaller than the second quantity of the fluid.

5. The medication injection device of claim 1, wherein determining, based on the data, whether the air shot event occurred while dispensing the fluid further comprises:
 detecting a threshold period of inactivity of the medication injection device;
 detecting a sequence of multiple fluid dispensing events following the threshold period of inactivity; and
 determining that a first one of the multiple fluid dispensing events immediately following the threshold period of inactivity is an occurrence of the air shot event.

6. The medication injection device of claim 1, wherein the dosage tracking system is further configured to sense a pressure inside the barrel and the data is indicative of the pressure, wherein determining, based on the data, whether the air shot event occurred while dispensing the fluid further comprises:
 measuring rates of change of the pressure inside the barrel during a sequence of fluid dispensing events including a first fluid dispensing event occurring prior to a second fluid dispensing event;
 comparing a first rate of pressure change during the first fluid dispensing event to a second rate of pressure change during the second fluid dispensing event; and
 determining that the first fluid dispensing event is an occurrence of the air shot event when the first rate of pressure change is greater than the second rate of pressure change.

7. The medication injection device of claim 1, wherein the dosage tracking system further includes an accelerometer configured to measure motion of the medication injection device and outputs an indication of the motion in the data, and wherein the controller includes additional logic that when executed by the controller causes the controller to perform further operations including:
 identifying a tapping motion of the medication injection device as a bubble dislodge event; and
 determining that a fluid dispensing event following the bubble dislodge event within a first threshold period of time is an occurrence of the air shot event.

8. The medication injection device of claim 1, wherein the controller includes additional logic that when executed by the controller causes the controller to perform further operations including:
 identifying a rolling motion of the medication injection device as a fluid mixing event; and
 determining that a fluid dispensing event following the fluid mixing event within a threshold period of time is an occurrence of the air shot event.

9. The medication injection device of claim 1, wherein the medication injection device includes at least one of an insulin pen or a syringe.

10. A method of tracking injections of a fluid delivered by a medication injection device, comprising:
 measuring dispensing events from the medication injection device with a dosage tracking system;
 sending ultrasonic signals with a transducer of the dosage tracking system through the fluid along a length of the medication injection device;
 receiving reflected ultrasonic signals with the transducer, wherein data output from the dosage tracking system is indicative of a time of flight between emission and receipt of the ultrasonic signals;
 tracking the data indicative of the dispensing events output from the dosage tracking system with a controller coupled to the dosage tracking system; and
 determining based on the data whether one or more of the dispensing events includes an air shot event, including:
  calculating a volume of fluid dispensed during each of the dispensing events based upon the time of flight of the ultrasonic signals; and
  determining that the air shot event occurred during one or more of the dispensing events based on whether the volume of fluid dispensed during each of the dispensing events is less than a threshold volume.

11. The method of claim 10, wherein the dosage tracking system includes an accelerometer, the method further comprising:
 measuring motion of the medication injection device with the accelerometer;
 identifying a tapping motion of the medication injection device as a bubble dislodge event; and
 determining that a next one of the dispensing events following the bubble dislodge event includes the air shot event.

12. The method of claim 11, further comprising:
 identifying a rolling motion of the medication injection device as a fluid mixing event; and
 determining that the next one of the dispensing events following the fluid mixing event and the bubble dislodge event includes the air shot event.

13. The method of claim 10, further comprising:
 calculating an orientation of the medication injection device with an orientation tracker included in the dosage tracking system, wherein the orientation of the medication injection device is included in the data received by the controller; and
 determining that the one or more dispensing events includes the air shot event based on the orientation of the medication injection device.

14. The method of claim 10, further comprising:
 measuring a period of inactivity of the medication injection device with the dosage tracking system; and
 determining based on the data that the one or more dispensing events includes an occurrence of the air shot event when the data indicates the period of inactivity exceeds a threshold period and is followed by one of the one or more dispensing events.

15. The method of claim 10, further comprising:
 measuring a pressure inside a barrel containing the fluid with the dosage tracking system during a sequence of the dispensing events including a first dispensing event and a second dispensing event, the first dispensing event occurring prior to the second dispensing event;
 comparing a first rate of pressure change during the first dispensing event to a second rate of pressure change during the second dispensing event based, at least in part, the measuring of the pressure; and
 determining that the first dispensing event includes the air shot event when the first rate of pressure change is greater than the second rate of pressure change.

16. The method of claim 10, further comprising:
 measuring velocities of the dispensing events with the dosage tracking system during a sequence of the dispensing events including a first dispensing event and a second dispensing event, the first dispensing event occurring prior to a second dispensing event, and wherein the velocities includes a first velocity during the first dispensing event and a second velocity during the second dispensing event;
 comparing the first velocity during the first dispensing event to the second velocity during the second dispensing event; and determining that the first dispensing event includes an occurrence of the air shot event when the first velocity is greater than the second velocity.

17. The method of claim 10, further comprising:
calculating, based on the data received by the controller, a quantity of medication dispensed to a patient by subtracting a quantity of the fluid dispensed during the air shot event from a total quantity of the fluid dispensed.

18. The method of claim 10, wherein at least one of the dispensing events includes at least one of dialing a dosage or dispensing a volume of fluid.

19. A medication injection device, comprising:
a plunger configured to fit, at least partially, within a barrel to dispense fluid from the barrel;
a dosage tracking system configured to output data indicative of an amount the fluid dispensed; and
a controller disposed within the medication injection device and coupled to the dosage tracking system to receive the data output from the dosage tracking system, wherein the controller includes logic that when executed by the controller causes the medication injection device to perform operations including:
determining, based on the data, whether an air shot event occurred while dispensing the fluid, including:
detecting a threshold period of inactivity of the medication injection device;
detecting a sequence of multiple fluid dispensing events following the threshold period of inactivity; and
determining that a first one of the multiple fluid dispensing events immediately following the threshold period of inactivity is the air shot event.

20. A medication injection device, comprising:
a plunger configured to fit, at least partially, within a barrel to dispense fluid from the barrel;
a dosage tracking system configured to output data indicative of an amount the fluid dispensed, wherein the dosage tracking system is further configured to sense a pressure inside the barrel and the data is indicative of the pressure; and
a controller disposed within the medication injection device and coupled to the dosage tracking system to receive the data output from the dosage tracking system, wherein the controller includes logic that when executed by the controller causes the medication injection device to perform operations including:
determining, based on the data, whether an air shot event occurred while dispensing the fluid, including:
measuring rates of change of the pressure inside the barrel during a sequence of fluid dispensing events including a first fluid dispensing event and a second fluid dispensing event, the first fluid dispensing event occurring prior to the second fluid dispensing event, wherein the rates of change of the pressure inside the barrel include a first rate of pressure change during the first fluid dispensing event and a second rate of pressure change during the second fluid dispensing event;
comparing the first rate of pressure change during the first fluid dispensing event to the second rate of pressure change during the second fluid dispensing event; and
determining that the first fluid dispensing event is an occurrence of the air shot event when the first rate of pressure change is greater than the second rate of pressure change.

21. A medication injection device, comprising:
a plunger configured to fit, at least partially, within a barrel to dispense fluid from the barrel;
a dosage tracking system configured to output data indicative of an amount the fluid dispensed, wherein the dosage tracking system is further configured to measure motion of the medication injection device and output an indication of the motion in the data; and
a controller disposed within the medication injection device and coupled to the dosage tracking system to receive the data output from the dosage tracking system, wherein the controller includes logic that when executed by the controller causes the medication injection device to perform operations including:
identifying, based on the data, a rolling motion of the medication injection device as a fluid mixing event; and
determining that a fluid dispensing event following the fluid mixing event within a threshold period of time is an occurrence of an air shot event.

22. At least one machine-accessible storage medium having stored thereon instructions, which when executed by a machine cause the machine to perform operations comprising:
measuring dispensing events of a fluid from a medication injection device with a dosage tracking system;
measuring a period of inactivity of the medication injection device with the dosage tracking system;
tracking data indicative of the dispensing events output from the dosage tracking system with a controller coupled to the dosage tracking system; and
determining based on the data whether one or more of the dispensing events includes an air shot event, including:
determining based on the data that the one or more dispensing events includes an occurrence of the air shot event when the data indicates the period of inactivity exceeds a threshold period and is followed by one of the one or more dispensing events.

23. At least one machine-accessible storage medium having stored thereon instructions, which when executed by a machine cause the machine to perform operations comprising:
measuring dispensing events of a fluid from a medication injection device with a dosage tracking system, including:
measuring a pressure inside a barrel containing the fluid with the dosage tracking system during a sequence of the dispensing events including a first dispensing event and a second dispensing event, the first dispensing event occurring prior to the second dispensing event;
tracking data, including the pressure, indicative of the dispensing events output from the dosage tracking system with a controller coupled to the dosage tracking system; and
determining based on the data whether one or more of the dispensing events includes an air shot event, including:
comparing a first rate of pressure change during the first dispensing event to a second rate of pressure change during the second dispensing event based, at least in part, on the pressure; and
determining that the first dispensing event includes the air shot event when the first rate of pressure change is greater than the second rate of pressure change.

24. At least one machine-accessible storage medium having stored thereon instructions, which when executed by a machine cause the machine to perform operations comprising:
- measuring dispensing events of a fluid from a medication injection device with a dosage tracking system, including:
  - measuring velocities of the dispensing events with the dosage tracking system during a sequence of the dispensing events including a first dispensing event and a second dispensing event, the first dispensing event occurring prior to the second dispensing event, and wherein velocities includes a first velocity during the first dispensing event and a second velocity during the second dispensing event;
- tracking data indicative of the dispensing events output from the dosage tracking system with a controller coupled to the dosage tracking system; and
- determining based on the data whether one or more of the dispensing events includes an air shot event, including:
  - comparing the first velocity during the first dispensing event to the second velocity during the second dispensing event; and
  - determining that the first dispensing event includes an occurrence of the air shot event when the first velocity is greater than the second velocity.

25. At least one machine-accessible storage medium having stored thereon instructions, which when executed by a machine cause the machine to perform operations comprising:
- measuring dispensing events of a fluid from a medication injection device with a dosage tracking system, including:
  - measuring motion of the medication injection device with an accelerometer;
- tracking data indicative of the dispensing events and the motion of the medication injection device output from the dosage tracking system with a controller coupled to the dosage tracking system; and
- determining based on the data whether one or more of the dispensing events includes an air shot event, including:
  - identifying a rolling motion of the medication injection device, based on the motion of the medication injection device as a fluid mixing event; and
- determining that a next one of the dispensing events following the fluid mixing event includes an occurrence of the air shot event.

* * * * *